United States Patent [19]

Sorensen

[11] Patent Number: 5,082,834

[45] Date of Patent: Jan. 21, 1992

[54] ANTI-INFLAMMATORY AND ANTI-ULCER COMPOUNDS AND PROCESS

[76] Inventor: John R. J. Sorensen, 1167 Hollywood Ave., Cincinnati, Ohio 45224

[21] Appl. No.: 585,027

[22] Filed: Sep. 18, 1990

Related U.S. Application Data

[60] Continuation of Ser. No. 786,727, Oct. 15, 1985, abandoned, which is a continuation of Ser. No. 604,728, Apr. 27, 1984, abandoned, which is a continuation of Ser. No. 109,097, Jan. 2, 1980, abandoned, which is a continuation of Ser. No. 910,421, May 30, 1978, Pat. No. 4,221,785, which is a division of Ser. No. 563,778, Mar. 31, 1975, abandoned.

[51] Int. Cl.$^5$ ............... A61K 31/60; A61K 31/555
[52] U.S. Cl. ........................... 514/159; 514/184; 514/186
[58] Field of Search ............... 514/159, 184, 186

[56] References Cited

PUBLICATIONS

Reprint from *Deutsche Medizinische Wochenschrift* (German Medical Weekly), Stuttgart, Jul. 4, 1952, "Treatment of Rheumatic Diseases with A Copper-Sodium Salicylate Compound (Permalon)", Hangarter et al.
*Zeitschrift fur Rheumaforschung*, 25:289–294, 1966, Hangarter.
*Med. Welt* 25(N.F.), 1968–1978, 1974, Hangarter.

*Primary Examiner*—Stanley J. Friedman
*Attorney, Agent, or Firm*—Wood, Herron & Evans

[57] ABSTRACT

Disclosed herein are anti-inflammatory and anti-ulcer copper coordination compounds and a process for using them in the treatment of arthritis and gastrointestinal ulcers in animal bodies. The copper coordination compounds utilized are the reaction products of copper salts with:

1. aromatic carboxylic acids or their alkaline earth salts;
2. heterocyclic carboxylic acids or their alkaline earth salts;
3. amino acids or their alkaline earth salts;
4. amines; and
5. suitably substituted steroids.

The process disclosed comprises administering to experimental animals, orally or parentrally (subcutaneously), in controlled dosages, the aforementioned copper coordination compounds for the treatment of inflammation (i.e., arthritis) and ulcers of the gastrointestinal tract.

9 Claims, No Drawings

ANTI-INFLAMMATORY AND ANTI-ULCER COMPOUNDS AND PROCESS

This application is a continuation of application Ser. No. 786,727, filed Oct. 15, 1985, abandoned; which is a continuation of Ser. No. 604,728, filed Apr. 27, 1984, abandoned; which is a continuation of Ser. No. 109,097, filed Jan. 2, 1980, abandoned; which is a continuation of Ser. No. 910,421, filed May 30, 1978, U.S. Pat. No. 4,221,785, granted Sept. 9, 1980; which is a division of Ser. No. 563,778, filed Mar. 31, 1975, abandoned.

BACKGROUND OF THE INVENTION

The prior art is replete with attempts to discover new anti-inflammatory drugs that are useful in the treatment of arthritis. Some of the more widely published results relate to the use of aspirin, indomethacin, penicillamine, hydrocortisone and dexamethasone. While all have demonstrated, to varying degrees, anti-inflammatory activity, they all exhibit undesirable side effects.

Such undesirable side effects include, for some of these drugs, toxicity problems; the production of fatty liver problems; and the creation of Cushing Syndrome For a further and more complete discussion see Bach, "Adverse Reactions of Antirheumatic Drugs", Int. J. Clin. Pharmacol 7 2/3 (1973) 198-205.

Of even more importance, all of the above anti-inflammatory drugs produce gastrointestinal ulceration in experimental animals and in humans. Volume VII, p. 160, Side Effects of Drugs, (1971 Excerpta Media, Amsterdam); G. L. Bach, "Adverse Reactions of Antirheumatic Drugs", supra. Insofar as the state of the art is concerned, it is widely recognized that "it has not been possible to dissociate gastrointestinal toxicity from anti-inflammatory activity." Side Effects of Drugs, supra at p. 100.

It is therefore the principal objectives of my invention to provide anti-inflammatory drugs for use in treating arthritis in experimental animals which exhibit improved anti-inflammatory activities while at the same time providing drugs that are anti-ulcergenic and have acceptable levels of toxicity.

SUMMARY OF THE INVENTION

It has been quite unexpectedly determined that copper coordination compounds produced by reacting copper salts with the following classes of organic compounds produce products which when used in accordance with the following processes, exhibit excellent anti-inflammatory activity in animals, i.e., a warm-blooded animal or mammalian subject, and which are anti-ulcer:

1. aromatic carboxylic acids or their alkaline earth salts;
2. heterocyclic carboxylic acids or their alkaline earth salts;
3. amino acids or their alkaline earth salts;
4. amines; and
5. suitably substituted steroids.

It has been empirically determined that the copper coordination compounds disclosed herein not only demonstrate excellent anti-inflammatory activity but that they are anti-ulcer and may be utilized both as anti-inflammatory agents in the treatment of arthritis and in the treatment of gastrointestinal ulcers in animals.

In the treatment of inflammation and/or ulcers, the compounds are administered orally or parentrally. The copper coordination compounds, being relatively insoluble in water, are administered by dissolving them in saline solution to which a suitable suspending agent has been added.

In treating inflammation by subcutaneously injecting test animals with the copper coordination compound so prepared it has been found that excellent anti-inflammatory results, in the test models hereinafter described, may be obtained if the dosages administered comprise about 2.5–165 mg. per kilogram of body weight.

In treating gastrointestinal ulcers by orally introducing into test animals the copper coordination compounds of this invention it has been found that excellent results, in the test models hereinafter described, are obtained if the dosages administered comprise about 2 to 125 mg. per kilogram of body weight.

DETAILED DESCRIPTION OF THE INVENTION

For the purpose of more fully understanding the present invention, a copper coordination compound is intended to mean a compound whose molecular structure contains one or more copper atoms bonded to one or more atoms of one or more molecules or ions by coordinate covalent bonds.

The copper coordination compounds of the present invention are prepared by reacting copper salts, preferably cupric chloride or cupric acetate with a member of the following classes of organic compounds:

1. aromatic carboxylic acids or their alkaline earth salts;
2. heterocycline carboxylic acids or their alkaline earth salts;
3. amino acids or their alkaline earth salts;
4. amines; and
5. suitably substituted steroids.

More specifically, it has been found that suitable compounds may be produced by reacting cupric chloride with the sodium salts of L & D tryptophan, anthranilic acid, 3,5-diisopropylsalicylic acid, acetylsalicylic acid, hydrocortisone-21-phosphate, dexamethasone-21-phosphate, salicylic acid, 3-p-chlorophenyl-3, 4, 5, 6,-tetrahydro-β-carboline-5-carboline-5-carboxylic acid, 3, 4, 5, 6-tetra-hydro-β-carboline-5-carboxylic acid, and 1-(p-chlorobenzoyl)-5-methoxy-2-methylindole-3-acetic acid; by reacting cupric chloride with 1-phenyl-5-aminotetrazole, ε aminocaproic acid, pyridine, a mixture of D and L-tryptophan, morpholine, and histamine; by reacting cupric chloride with the ammonium salt of hydrocortisone-21-hemisuccinic acid; by reacting cupric acetate with the sodium salts of 2[3(trifluoromethyl)phenyl] aminonicotinic acid (sometimes referred to hereinafter as tpan), 1-carboxyisoquinoline, phenylcinchoninic acid, hydrocortisone-21-phosphate, and 4-n-butyl-1,2-diphenyl-3,5-pyrazolidinedione; by reacting cupric acetate with the ammonium salt of nicotinic acid; by reacting cupric acetate with D-pencillamine, 1-phenyl-5-aminotetrazole, D or L-aspartic acid, L-lysine, 2-carboxyindole; and by reacting cupric acetate with the potassium salt of 17-hydroxy-3-oxo-17α-pregn-4,6-diene-21 carboxylic acid.

It is preferable to produce copper coordination solvates rather than anhydrous compounds as will be more fully appreciated by the following description. The compounds may be solvated with a lower alcohol (methanol or ethanol), acetone, pyridine, water or dimethyl sulfoxide.

Following is a more detailed description of how the copper coordination compounds of the present invention may be prepared. Table V contains suggested structural formulae for some of my coordination compounds. Not all have been empirically determined.

EXAMPLE 1

Bis-L-tryptophanato(O,N)copper(II),[Cu(II)(L-tryptophan)$_2$]

L-tryptophan (5.0 g, 0.025 mol) was dissolved in 100 ml of H$_2$O with a solution of NaOH (50%), filtered and back titrated if necessary with a solution of HCl (10%) until indicator paper showed the solution to be weakly basic. This solution was then dropped into 100 ml of H$_2$O containing CuCl$_2$ dihydrate (3.3 g, 0.021 mol). After stirring for about one hour a precipitate formed and was collected by filtration. This blue precipitate was washed with H$_2$O and diethylether, dried at 100° and 15 mm Hg overnight and weighed (4.7 g, 82% yield). A sample of this material on heating turned brown at 240° C. and finally decomposed at 260° C. Analysis Calcd. for C$_{22}$H$_{22}$N$_4$O$_4$Cu: C, 56.22; H, 4.72; N, 11.92. Found: C, 56.07; H, 4.89 and N, 12.16.

EXAMPLE 2

Bis-D-tryptophanato(O,N)copper(II)[Cu(II)(D-tryptophan)$_2$]

This coordination compound was prepared as described for the L isomer (example 1) using 5.0 g, 0.021 mol of D-tryptophan. After collecting the precipitate by filtration, washing with H20, diethylether and acetone (250 ml), the precipitate was dried overnight at 100° and 15 mm Hg and weighed (4.3 g, 75% yield). A sample of this material decomposed slowly on heating to 269° C. Analysis Calcd. for C$_{22}$H$_{22}$N$_4$O$_4$Cu: C, 56.22; H, 4.72; N, 11.92. Found: C, 56.10, H, 4.72 and N, 12.00.

EXAMPLE 3

Bisanthranilato(O,N)copper(II),[Cu(II)(anthranilate)$_2$]

The sodium salt of anthranilic acid (5 g 0.04 mol) was prepared as described in example 1 in 150 ml of H$_2$O with 50% NaOH. This solution was dropped into 300 ml of a stirred aqueous solution of CuCl$_2$ dihydrate (2.5 g, 0.016 mol). The precipitate which formed was removed by filtration and washed with H$_2$O and diethylether (5×50 ml). After drying overnight @120° C. and 15 mm Hg the material weighed 6.1 g, 99% yield. A sample of this greenish-blue material decomposed on heating to 240° C. and continued to decompose on heating to 290° C. Analysis Calcd. for C$_{14}$H$_6$N$_2$O$_4$Cu: C, 50.07; H, 3.60; N, 8.35. Found: C, 50.07; H, 3.77; N, 8.42.

EXAMPLE 4

Bis(3,5-diisopropylsalicylato(O,O)copper(II)[Cu(II)(3,5-dips)$_2$]

A solution of the sodium salt of 3,5-diisopropylsalicylic acid (5 g, 0.023 mol) was prepared as described in example 1 and added to 300 ml of a stirred aqueous solution of CuCl$_2$ dihydrate (1.59 g, 0.0336 mol). A brown precipitate formed which when recrystallized from ether gave green crystals These crystals were filtered and dried at 125° C. and 15 mm Hg for three hours. The resulting brown crystalline material melted with decomposition over the range of 142°–144° C. Analysis Calcd. for C$_{26}$H$_{34}$O$_3$Cu: C, 61.70; H, 6.77. Found: C, 61.49; H, 6.83.

EXAMPLE 5

Tetraμ-acetylsalicylato)biscopper(II),[Cu(II)$_2$(aspirinate)$_4$]

The sodium salt of acetylsalicylic acid was prepared by dissolving acetylsalicylic acid (30 g, 0.165 mol) in 200 ml of H$_2$O at 0° C. with 50% NaOH so that the pH did not go above 11.0 and rarely reached 11.0. This was done over a period of 45 to 60 minutes. The final pH of the solution was about 8.7. The CuCl$_2$ solution prepared by adding 56.5 g, 0.330 mol of CuCl$_2$ dihydrate to 500 ml of water, was added to a stirred solution of sodium acetylsalicylate during a period of 10 to 15 minutes. Following the completion of this addition the blue precipitate was collected by filtration; washed with H$_2$O (500 ml×2), acetone (400 ml×2) and diethlether (300 ml) and left to dry on a filter funnel attached to a water aspirator. After two days the powder was dried at 50° C. for 6–7 hours and weighed (31.3 g, 90.6% yield). Analysis calculated for : C$_{36}$H$_{28}$O$_{16}$Cu$_2$: C, 51.25; H, 3.35; Found: C, 51.20; H, 3.51.

EXAMPLE 6

[2[3(trifluoromethyl)phenyl]aminonicotinato]$_{2n}$-(aqua)$_n$-copper(II)$_n$,[Cu(II)$_n$(tpan)$_{2n}$(H$_2$O)$_n$]

The sodium salt of 2[3(trifluoromethyl)pheynl] aminonicotinic acid (20 g, 0.0708 mol) was prepared as described in example 1. The solution of this salt was then added to about 300 ml of a saturated, stirred solution of cupric acetate monohydrate. The resultant greenish precipitate was collected by filtration and dissolved in 200 ml of diethylether. The ether solution was then dropped into about 4 liters of boiling skellysolve A. The resultant precipitate was collected from the hot solution by filtration, dried at 125° C. for three hours at 15 mm Hg and weighed (16 g, 70% yield). A sample of this material melted with decomposition over the range of 201 to 208° C. Analysis Calcd. for C$_{52}$H$_{36}$O$_{10}$N$_8$F$_{12}$Cu: C, 48.49; H, 2.82; N, 8.70. Found: C, 48.53; H, 2.66; N, 8.91.

EXAMPLE 7

D-penicillaminato-(aqua)$_{1.5}$-copper(I),[Cu(I)$_n$(D-pen)$_n$(H$_2$O)$_{1.5n}$]

D-penicillamine (5 g, 0.0335 mol) was dissolved in 50 ml of water. The solid cupric acetate monohydrate (6.68 g, 0.017 mol) was then added to the solution at such a rate so as to not exceed its rate of solution. Upon the completion of this addition the solution was dark gray. About 50–100 ml of H$_2$O was then added and the mixture left to stir for about 30 minutes. The resultant gray precipitate was collected by filtration leaving a blue filtrate (125 ml). This blue filtrate was subsequently diluted with about 375 ml of acetone and set aside for use in example 8. The airdried gray powder weighed 4.3 g, 54.0% yield. A sample of this material decomposed over the range of 155°–157° C. Analysis Calcd. for C$_5$H$_9$SNO$_{3.5}$Cu: C, 25.26; H, 5.10, N, 5.89. Found: C, 25.32; H, 5.03; N, 5.47.

EXAMPLE 8

(D-penicillaminato)$_{2n}$-(aqua)$_{2n}$-copper(II),[Cu(II)$_n$(D-pen)2n]

On standing, the acetone diluted blue filtrate described in the preparation of Example 7 gave a gray precipitate which was collected by filtration and this filtrate also set aside. The gray solid was washed with 60 ml of water and the remaining light tan solid washed with 60 ml of acetone air dried and weighed (1.15 g, 17.4% yield). A sample of this solid melted with decomposition over the range of 155 to 157° C. Analysis $C_{10}H_{24}O_6S_2N_2Cu$: C, 30.33; H, 6.11; N, 7.08. Found: C, 30.42; H, 6.49; N, 6.72.

EXAMPLE 9

(D-pencillamine disulfide)$_n$-(aqua)$_{3n}$copper(II)$_n$, [Cu(II)$_n$(D-pen disulfide)$_n$(H$_2$O)$_{3n}$]

The acetone-water filtrate, obtained after removing example 8 from the blue acetone filtrate, described above, was concentrated to about 100 ml and diluted with 400 ml of acetone. A blue precipitate (1.3 g, 9.4% yield) was obtained following filtration, washing with acetone and air drying. A sample of this material decomposed over the range of 157° to 158° C. After drying twice at 73° and 15 mm Hg overnight a sample of this material decomposed over the range of 173° to 175° C. Analysis Calcd. for $C_{10}H_{24}N_2S_2O_7Cu$: C, 29.15; H, 5.87; N, 6.80. Found: C, 29.43; H, 5.76; N, 6.36.

EXAMPLE 10

(Acetato)$_{2n}$-(1-phenyl-5-aminotetrazolato)$_n$-copper-(II)$_n$, [Cu(II)$_n$(pat)$_n$(acetate)$_{2n}$]

Five grams of cupric acetate monohydrate (0.012 mol) was dissolved in 20 ml of H$_2$O. This solution was diluted with 100 ml of methanol. 5 g (0.31 mol) of 1-phenyl-5-aminotetrazole was added to obtain a blue gel. This gel was filtered and the resulting blue flakes were washed with about 400 ml of methanol until the washings were no longer blue. The filtrate was then concentrated to about 150 ml and stored for about one week in the refrigerator. A precipitate formed and was removed by filtration. This green crystalline solid was air dried and weighed (3.8 g, 17.9% yield). A sample of this solid decomposed over the range of 186°–189° C. Analysis Calcd. for $C_{22}H_{26}N_{10}O_8Cu_2$: C, 38.54; H, 3.82; N, 20.43. Found: C, 38.42; H, 3.94; N, 20.92.

EXAMPLE 11

(1-phenyl-5-aminotetrazolato)$_{2n}$-(chloride)$_{2n}$-copper (II)$_n$·[Cu(II)$_n$(pat)$_{2n}$(HCl)$_{2n}$]

Five grams (0.012 mol) of 1-phenyl-5-aminotetrazole was dissolved in 30 ml of methanol, then 5 g (0.029 mol) of CuCl$_2$ dihydrate dissolved in 25 ml of methanol was added to the stirred solution of tetrazole. The resulting solution was filtered and set aside. Three subsequent crops of a green solid were obtained following filtration and concentration of the filtrate. The combination of these were air dried and weighed (5 g, 17.7% yield). A sample of this material decomposed on heating over the range of 184° to 185° C. Analysis Calcd. for $C_{14}H_{14}N_{10}CuCl_2$: C, 36.81; H, 3.09; N, 30.67. Found: C, 36.65; H, 3.17; N, 31.03.

EXAMPLE 12

(D-Aspartato)$_n$(aqua)$_{3.5n}$-copper(II)$_n$, [Cu(II)$_n$(D-aspartate)$_n$(H$_2$O)$_{3.5n}$]

This material is made in a manner similar to the preparation of example 1 using D-aspartic acid in place of L-tryptophan. Analysis calculated for $C_4H_{12}N\ O_{7.5}Cu$: C, 18.69; H, 4.66. Found: C, 18.55; H, 4.92.

EXAMPLE 13

(L-Aspartato)$_n$-(aqua)$_{3.5n}$-copper(II)$_n$, [Cu(II)$_n$(L-aspartate)$_n$(H$_2$O)$_{3.5n}$]

This material is made in a manner similar to the preparation of example 1 using L-aspartic acid in place of L-tryptophan. Analysis calculated for $C_4H_{12}N\ O_{7.5}Cu$: C, 18.69; H, 4.66. Found: C, 18.41; H, 4.73.

EXAMPLE 14

(L-Lysino)$_n$-(chloro)$_{2n}$-(aqua)$_n$-copper (II)$_n$, [Cu(II)$_n$·(L-lysinate)$_n$(Cl)$_{2n}$(H$_2$O)$_n$]

This material is made in a manner similar to example 1 using L-lysine in place of L-tryptophan. A sample of this material decomposed on heating over the range of 169° to 170° C. Analysis calculated for $C_6H_{16}O_3CuCl_2$: C, 24.10; H, 5.40; Cl, 23.70; N, 9.38. Found: C, 24.54; H, 5.07; Cl, 24.00 N, 9.36.

EXAMPLE 15

(L-Lysino)$_{2n}$-(chloro)$_{2n}$-(aqua)$_n$-copper(II)$_n$,[Cu(II)$_n$(L-lysinate)$_{2n}$(Cl)$_{2n}$(H$_2$O)$_n$]

This material is made in a manner similar to example 1 using L-lysine in place of L-tryptophan. A sample of this compound decomposed on heating up to and over the range 210° to 214° C. Analysis calculated for $C_{12}H_{32}N_4O_5CuCl_2$: C, 32.40; H, 6.80; Cl, 12.60. Found: C, 32.56; H, 7.04; Cl, 12.24.

EXAMPLE 16

Bis(D,L-tryptophanato(O,N)copper(II),[Cu(II)(D,L-tryptophan)$_2$]

This coordination compound was prepared and isolated as described in example 1 using a mixture of D and L-tryptophan in place of L-tryptophan. Analysis Calcd. for $C_{22}H_{22}N_4O_4Cu$: C, 56.22; H, 4.72. Found: C, 55.58; H, 4.87.

EXAMPLE 17

($\epsilon$-aminocaproato)$_n$-(chloro)$_{1.5n}$-(methanol)$_{0.5n}$-copper (II)$_n$,[Cu(II)$_n$($\epsilon$-aminocaproate)$_n$(Cl)$_{1.5n}$(CH$_3$OH)$_{0.5n}$ This coordination compound was prepared by stirring a suspension of 10 g (0.08 mol) of $\epsilon$-aminocaproic acid in 200 ml of methanol and slowly adding 10 g (0.065 mol) of solid cupric chloride dihydrate. The resultant green precipitate was collected by filtration washed with methanol, dried at 25° C. and 15 mm Hg overnight, and weighed 10.5 g, 51% yield). A sample of this material decomposed over the range of 157° to 158° C. Analysis Calcd. for $C_7H_{15.5}O_{2.5}CuCl_{1.5}$: C, 29.53; H, 5.91; Cl, 20.11. Found: C, 29.97; H, 6.06; Cl, 20.36.

EXAMPLE 18

($\epsilon$-aminocaproato)$_n$-(chloro)$_{2n}$-(aqua)$_{0.5n}$-copper(II)$_n$, [Cu(II)$_n$($\epsilon$-aminocaproate)$_n$(Cl)$_{2n}$(H$_2$O)$_{0.5n}$]

This coordination compound was obtained from the filtrate described in example 17. Following concentration of the filtrate and methanol washings to about 100 ml of bluish-green precipitate formed. This precipitate was collected by filtration dried at 25° C. at 15 mm Hg and weighed (4.6 g, 21% yield). A sample of this material decomposed on heating over the range of 193° to 194° C. Analysis Calcd. for $C_6H_{14}NO_{2.5}Cl_2Cu$ C, 26.24; H, 5.14; Cl, 25.82. Found: C, 26.29; H, 5.28; Cl, 25.39.

EXAMPLE 19 tetra(μ-acetato)bis(monopyridino)copper(II),[Cu(II)$_n$-(pyridine)$_n$(acetate)$_{2n}$]

This coordination compound was prepared by adding 10 g (0.025 mol) of cupric acetate monohydrate to 70 ml of pyridine and the mixture heated while stirring at 100° C. The hot suspension was filtered and the resulting precipitate collected by filtration and washed with 200 to 300 ml of diethylether. A sample of this green solid decomposed on heating over the range of 214° to 216° C. When the ether-pyridine filtrate cooled a second precipitate, which was bluish, was obtained. Removal by filtration and washing with ether gave a second crop of the green material in the filtrate. This green solid had a decomposition range of 216 to 218° C. A mixture decomposition range of 216° to 218° C. was observed for a sample of the combination of the two green solids. Total yield was 12 g, 92%. Analysis Calcd. for $C_{18}H_{22}N_2O_8Cu_2$: C, 41.46; H, 4.25; N, 5.37. Found: C, 41.87; H, 4.54; N, 5.23.

EXAMPLE 20

Bispyridinobischlorocopper(II),[Cu(II)(pyridine)$_2$(Cl)$_2$]

This composition was prepared by dissolving 9.42 g (0.062 mol) of $CuCl_2$ dihydrate in 95% ethanol and adding 15 g (0.19 mol) of pyridine slowly to the stirred solution. The resultant blue precipitate was removed by filtration, washed with 95% ethanol (200 ml), dried at about 50° C. for 24 hours and weighed (19.8 g, 35.6% yield). A sample of this material decomposed over the range of 225° to 275° C. Analysis Calcd. for $C_{10}H_{10}N_2CuCl_2$: C, 41.32; H, 3.44. Found: C, 41.25; H, 3.52.

EXAMPLE 21

Bismorpholoniumtetrachlorocopper(II),[Cu(II)(morpholine)$_2$(Cl)$_2$(HCL)$_2$]

This coordination compound was prepared according to the published procedure of W. H. C. Rueggeberg, G. N. Jarman and R. B. Wearn, J.A.C.S., 69, 1222 (1947) incorporated by reference herein. Starting with 14.5 g (0.167 m morpholine the coordination compound was obtained in 41% yield. A sample of this green crystalline melted with decomposition over the range of 167°–170° C. Analysis Calcd. for $C_8H_{20}N_2O_2CuCl_4$: C, 25.17; H, 5.28; N, 7.34. Found: C, 25.17; H, 5.41; N, 7.21.

EXAMPLE 22

(Histamino)$_n$-(chloro)$_{2n}$-(hydrochloro)$_{2n}$-copper(II)$_n$, Cu(II)$_n$(histamine)$_n$(Cl)$_{2n}$(HCl)$_{2n}$]

This coordination compound was prepared by mixing 5 g (0.048 mol) of cupric chloride dihydrate in 200 ml of methanol and concentrating to 135 ml. On standing a tan solid precipitated. This was removed by filtration and the filtrate concentrated to 80 ml. Upon addition of 40 ml of diethylether to this concentrate a light green solid precipitated. After removal by filtration and air drying this material was weighed (4.0 g, 23% yield). A sample decomposed over the range of 185° to 189° C. with softening at 182° C. Analysis Calcd. for $C_5H_{10}N_3Cl_4Cu$: C, 18.91; H, 3.17; N, 13.24. Found: C, 18.90, H, 3.30; N, 13.30.

EXAMPLE 23

(Sodium)$_4$-(salicylato)$_4$-copper (II)$_2$, [Cu(II)$_2$(salicylate)$_4$(Na)$_4$]

This material was prepared from the material obtained in example 24 with the addition of sodium ethoxide in suitable solvent. Analysis calculated for $C_{28}H_{16}O_{12}Cu_2Na_4$ were found to be within ±0.4% of the theoretical values.

EXAMPLE 24

(Salicylato)$_{2n}$-(aqua)$_{4n}$-copper(II)$_n$, [Cu(II)(Salicylate)$_2$(H$_2$O)$_4$]

This material may be prepared as described in example 1 using salicylic acid in place of L-tryptophan. Analysis calculated for $C_{14}H_{18}O_{10}Cu$: C, 41.03; H, 4.43. Found: C, 41.24; H, 4.52.

EXAMPLE 25

(Pyridine-3-carboxylato)$_{2n}$-(aqua)$_{1.5n}$-copper (II), [Cu(II)$_{2n}$(nicotinate)$_{4n}$(H$_2$O)$_{3n}$]

This coordination compound was prepared by dissolving 10 g (0.08 mol) nicotinic acid in 100 ml of water with concentrated $NH_4OH$ so that the final pH was 7.0. A cupric chloride solution, prepared by dissolving 21.6 g (0.14 mol) of cupric chloride dihydrate in 200 ml of water, was stirred while the ammonium salt of nicotinic acid was added dropwise. The blue precipitate was collected by filtration, washed with 500 ml of water and air dried. The resulting material was dried at 80° C. and weighed (10.7 g, 80% yield). A sample of this material decomposed on heating up to and through the range of 265° to 266° C. Analysis Calcd. for $C_{24}H_{22}O_{11}N_4Cu_2$: C, 43.05; H, 3.31; N, 8.37. Found: C, 43.25; H, 3.00; N, 8.12.

EXAMPLE 26

(Isoquinoline-1-carboxylato)$_{2n}$-copper (II)$_n$, [Cu(II)$_n$(1-carboxyisoquinoline)$_{2n}$]

The copper coordination compound of 1-carboxyisoquinoline (5 g 0.029 mol) was prepared by adding to its solution of the sodium salt, prepared as in example 1 in 200 ml of water using 1-carboxyisoquinoline in place of L-tryptophan, 60 ml of a saturated aqueous solution of cupric acetate monohydrate. The resultant purple precipitate was collected by filtration, washed with 500 ml of water and dried overnight at 100° C. and 15 mm Hg. A sample of this material (4.0 g, 70.2% yield) decomposed over the range of 295° to 296° C. Analysis Calcd. for $C_{20}H_{12}N_2O_4Cu$: C, 58.84; H, 2.97; N, 6.87. Found: C, 58.49; H, 3.14; N, 6.79.

EXAMPLE 27

(2-Phenyl-4-isoquinoline-carboxylato)$_{2n}$-(aqua)$_{2n}$-copper (II)$_n$·[Cu(II)$_n$(2-phenyl-4-carboxyisoquinoline)$_{2n}$(-H$_2$O)$_{2n}$]

This coordination compound was synthesized from the sodium salt of phenylcinchoninic acid (25 g, 0.15 mol), which was prepared as described in example 1 using "2-phenyl-4-isoquinolinecarboxylic acid" in place of L-tryptophan in 550 ml of water. The solution of the sodium salt was dropped into a stirred solution of cupric chloride dihydrate (14.2 g, 0.09 mol). The resulting green precipitate was collected by filtration, washed with methanol, water and then air dried and weighed (29.5 g, 67% yield). A sample of this material decomposed on heating over the range of 228° to 229° C. Analysis Calcd. for $C_{64}H_{48}N_4O_{12}Cu_2$: C, 64.48; H, 4.06; N, 4.70. Found: C, 64.55; H, 3.80; N, 4.61.

EXAMPLE 28

(Indole-2-carboxylato)$_{3n}$-(acetato)phd n-(aqua)$_{0.5n}$, [Cu(II)$_n$(2-carboxyindole)$_{3n}$(acetate)$_n$(H$_2$O)$_{0.5n}$]

This copper coordination compound was prepared from the parent acid 2-carboxyindole (4.5 g, 0.028 mol) as in example 1, using cupric acetate. The green precipitate was collected by filtration, air dried for several days, suspended in boiling methanol and again collected by filtration. It was then dried at 100° C. and 15 mm Hg overnight and at 125° and 15 mm Hg for 3 hours. A sample of this material (3.0 g, 23.3% yield) decomposed over the range of 249°-255° C. Analysis Calcd. for $C_{29}H_{22}N_3O_9Cu$: C, 56.91; H, 3.59; N, 6.86. Found: C, 56.87; H, 4.03; N, 6.62.

EXAMPLE 29

(Indole-2-carboxylato)$_{3n}$-(acetato)$_n$-(aqua)$_{3.5n}$, [Cu(II)$_n$(2--carboxyindole)$_{3n}$(acetate)$_n$(H$_2$O)$_{0.5n}$]

This material was prepared as described in example 1 using 2-carboxyindole in place of L-tryptophan and dried at 100° C. and 15 mm Hg over the weekend. A sample of this material did not melt but did turn brown, as did the material in example 28, on heating to 260°. Analysis Calcd. for $C_{29}H_{28}N_3O_{12}Cu$: C, 52.29; H, 4.20; N, 6.30. Found: C, 51.85; H, 3.78; N, 6.59.

EXAMPLE 30

(3-p-chlorophenyl-3,4,5,6-tetrahydro-β-carboline-5-carboxylato)$_{2n}$-(aqua)$_{2n}$-copper(II)$_n$, [Cu(II)$_n$(cp-tcca)$_{2n}$(H$_2$O)$_{2n}$]

The copper coordination compound of the parent acid (5 g, 0.015 mol) was prepared as described for example 1 except 3-p-chlorophenyl-3,4,5,6-tetrahydro-β-carboline-5-carboxylic acid was substituted for L-tryptophan. An olive drab precipitate was collected by filtration, washed with 500 ml of H$_2$O, 300 ml of diethylether and then with acetone until the washings were colorless. This material was dried at 100° C. overnight and 100° C. at 15 mm Hg for 3 hours before dissolving in acetone and precipitated with Skellysolve B. This material (2 g, 40% yield) was then dried overnight at 60° C. and 15 mm Hg and again at 125° C. and 15 mm Hg. A sample of this material decomposed over the range of 205° to 210° C. Analysis Calcd. for $C_{36}H_{32}Cl_2N_4O_6Cu$: C, 57.56; H, 4.30; N, 7.46. Found: C, 57.16; H, 4.15; N, 6.96.

EXAMPLE 31

(3,4,5,6-Tetrahydro-β-carboline-5-carboxylato)$_{2n}$(aqua)$_{2.5n}$-copper(II)$_n$·[Cu(II)$_n$(tcca)$_{2n}$(H$_2$O)$_{2.5n}$]

The copper coordination compound of the parent acid (5 g, 0.023 mol) was prepared as described for example 1 except that 3,4,5,6-tetrahydro-β-carboline-5-carboxylic acid was substituted for L-tryptophan. This dark green solid was washed with 500 ml of water, then suspended in 500 ml of boiling acetone and collected by filtration. Drying was done at 100° C. at atmospheric pressure for 24 hours and then at 110° C. and 15 mm Hg for 3 hours. Subsequent leaching with hot propylene glycol gave an insoluble material (3.3 g, 52.8% yield) which rapidly decomposed on heating to 294° C. Analysis Calcd. for $C_{24}H_{27}N_4O_{6.5}Cu$: C, 53.47; H, 5.05 and N, 10.40. Found: C, 53.54; H, 4.69 and N, 10.58.

EXAMPLE 32

(Hydrocortisone-21-phosphato)$_{2n}$-(aqua)$_{9n}$-copper-(II)$_{3n}$·[Cu(II)$_{3n}$(HC-21-phosphate)$_{2n}$(H$_2$O)$_{9n}$]

This coordination compound was prepared by dissolving 1 g (0.002 mol) of the disodium salt of hydrocortisone-21-phosphate in 25 ml of water and adding this solution dropwise to a stirred solution of cupric acetate monohydrate, prepared by adding 0.79 g (0.004 mol) of cupric acetate monohydrate to 25 ml of water. After the addition was complete, stirring was continued for one-half hour before the light blue precipitate was collected by filtration and washed with 500 ml of water before air drying. The yield was 0185 g, 34%. On heating a sample of this material to 209° C. it decomposed. Analysis Calcd. for $C_{42}H_{78}O_{25}P_2Cu_3$: C, 40.82; H, 6.36. Found: C, 40.59; H, 6.18.

EXAMPLE 33

(Hydrocortisone-21-phosphato)$_{2n}$-(aqua)$_{7n}$-copper (II)$_{3n}$· [Cu(II)$_{3n}$(HC-21-phosphate)$_{2n}$(H$_2$O)$_{7n}$]

This coordination compound was prepared by dissolving 1 g (0.002 mol) of the disodium salt of hydrocortisone-21-phosphate in 100 ml of water, adding 1 drop of concentrated hydrochloric acid to give a pH of 6.6 and adding this solution dropwise to a stirred solution of cupric chloride dihydrate (1 g, 0.006 mol) in 50 ml of water. After the addition was complete the mixture was allowed to stir for one hour and the light blue precipitate collected by filtration, washed with 200 ml of water, air dried and weighed (400 mg, 33% yield). A sample of this material gradually decomposed on heating to 210° C. Analysis Calcd. for $C_{42}H_{74}O_{23}P_2Cu_3$: C, 42.05; H, 6.22. Found: C, 42.00; H, 6.21.

EXAMPLE 34

(Hydrocortisone-21-hemisuccinato)$_{4n}$-(aqua)$_{6n}$-copper (II)$_{2n}$·[Cu(II)$_{2n}$(HC-21-hemisuccinate)$_{4n}$(H$_2$O)$_{6n}$]

This coordination compound was prepared by dissolving 1 g (0.002 mol) of hydrocortisone-21-hemisuccinic acid in 250 ml of water with concentrated ammonium hydroxide. The resulting pH was 9.0 and was adjusted to pH 7.0 with a 10% solution of hydrochloric acid. This solution was then added dropwise to a stirred solution of cupric chloride dihydrate (1g, 0.006 mol) dissolved in 250 ml of water. The resulting light blue-green precipitate was collected, air dried and weighed (1 g, 96% yield). A sample of this material decomposed on heating over the range of 191° to 195° C. Analysis Calcd. for $C_{100}H_{144}O_{38}Cu_2$: C, 57.71; H, 6.97. Found: C, 57.41; H, 7.26.

EXAMPLE 35

(Hydrocortisone-21-hemisuccinato)$_{4n}$-(aqua)$_{7n}$-copper (II)$_{2.5n}$[Cu(II)$_{2.5n}$(HC-21-hemisuccinato)$_{2n}$(H$_2$O)$_{7n}$]

This coordination compound was prepared by dissolving 1 g (0.002 mol) of hydrocortisone-21-hemisuccinic acid in 20 ml of water with concentrated ammonium hydroxide. The resulting pH was 9.5. This solution was then added dropwise to a stirred solution of cupric chloride dihydrate (1 g, 0.006 mol) dissolved in 15 ml of water. The light blue precipitate which formed was collected by filtration, air dried and weighed (1.2 g, 99% yield). A sample of this material decomposed on heating over the range of 196° to 197° C. Analysis Calcd. for $C_{100}H_{160}O_{46}Cu_5$: C, 49.71; H, 6.68. Found: C, 49.92; H, 6.63.

EXAMPLE 36

(9α-Fluoro-11β, 17α, 21-trihydroxy-16α-methyl-1,4-pregnadiene-3,20-dione-21-phosphato)$_{2n}$-(aqua)$_{7n}$-copper(II)$_{3n'}$ [Cu(II)$_{3n}$(dexamethasone-21-phosphate)$_{2n}$(H$_2$O)$_{7n}$]

This coordination compound was prepared by dropping a solution of the disodium salt of dexamethasone-21-phosphate (9 g, 0.017 mol) dissolved in 100 ml of water, into a stirred solution of 100 ml of water containing 4.6 g (0.003 mol) of cupric chloride dihydrate. After the addition was completed an additional 300 ml of water was added. The resulting light blue precipitate was collected by filtration, washed with water, air dried and weighed (8.1 g, 75% yield). A sample of this material gradually decomposed on heating to 300° C. Analysis Calcd. for $C_{88}H_{140}O_{46}P_4F_4Cu_6$: C, 42.02; H, 5.61. Found: C, 42.04; H, 5.5

EXAMPLE 37

(9α-Fluoro-11β, 17α-21-trihydroxy-16α-methyl-1,4-pregnadiene-3,20-dione-21-phosphato)$_{2n}$-(aqua)$_{1.5n}$-copper(II)$_{3n'}$ [Cu(II)$_{3n}$(dexamethasone-21-phosphate)$_{2n}$(H$_2$O)$_{1.5n}$]

This coordination compound was prepared by taking 2 g (0.0008 mol) of the material prepared in example 36 and suspending it in a stirred methanol for two hours to remove some of the water of hydration. After air drying this material was dried at 45° C. and 15 mm Hg overnight. A sample of this material also decomposed on heating to 300° C. Analysis Calcd. for $C_{88}H_{118}O_{35}P_4F_4Cu_6$: C, 45.62; H, 5.13. Found: C, 45.51; H, 5.48.

EXAMPLE 38

[1-(p-Chlorobenzoyl)-5-methoxy-2-methylindole-3-acetato]$_{4n}$-(aqua)$_{4n}$-copper(II)$_{2n'}$Cu(II)$_{2n}$[1-(p-chlorobenzoyl)-5-methoxy-2-methylindole-3-acetate]$_{4n}$(H$_2$O)$_{4n}$ This coordination compound was synthesized from the sodium salt of the parent acid (5 g, 0.014 mol), prepared as in example 1 except 1-(p-chlorobenzoyl)-5-methoxy-2-methylindole-3-acetic acid was used in place of L-tryptophan, in 200 ml of water. The solution of the sodium salt was dropped into a stirred 300 ml water solution of cupric chloride dihydrate (1.95 g, 0.013 mol). The resultant green precipitate was collected by filtration, washed with water, air dried and weighed (5.6 g, 98% yield). A sample of this material decomposed on heating to 190° C. Analysis Calcd. for $C_{76}H_{68}O_{20}N_4Cl_4Cu_2$: C, 56.13; H, 4.21; N, 3.44. Found: C, 56.00; H, 3.78; N, 3.40.

EXAMPLE 39

[1-(p-Chlorobenzoyl)-5-methoxy-2-methylindole-3-acetato]$_{4n}$-(acetone)$_{2n}$-copper(II)$_{2n'}$Cu(II)$_{2n}$[1-p-chlorobenzoyl)-5-methoxy-2-methylindole-3-acetate]$_{4n}$(CH$_3$COCH$_3$)$_{2n}$ This coordination was prepared in a manner similar to that described for example 38, using twice the amount of parent acid and cupric chloride dihydrate. However, after the green precipitate was collected by filtration it was leached with 1 liter of acetone and the leachate concentrated to 500 ml. On standing, additional green cyrstals formed in the acetone solution.

These were collected by filtration, air dried and weighed (6.9 g, 62% yield). A sample of this material decomposed on heating up to and over the range of 190° to 193° C. Analysis Calcd. for $C_{82}H_{72}O_{18}N_4Cl_4Cu_2$: C, 58.81; H, 4,79; N, 3.21. Found: C, 58.96; H, 4.34; N, 3.35.

EXAMPLE 40

(4-n-Butyl-1,2-diphenyl-3,5-pyrazolidinedione)$_{2n}$-copper(II)$_{n'}$[Cu(II)$_n$(4-n-butyl-1,2-diphenyl-3,5-pyrazolidinedione)$_{2n}$]

A solution of the sodium salt of the parent compound 4-n-butyl-1,2-diphenyl-3,5-pyrazolidinedione, (5 g, 0.015 Mol) dissolved in 50 ml of 95% ethanol was diluted with 150 ml of H$_2$O. To this stirred solution was added 2.73 g (0.007 mol) of cupric acetate monohydrate, in small aliquats. The greenish precipitate which formed was collected by filtration, dried at 95° C. and 15 mm Hg overnight and weighed (4.5 g, 94.5% yield). a sample of this material softened and melted over the range of 65° to 75° C. Analysis Calcd. for $C_{38}H_{38}N_4O_4Cu$: C, 67.29; H, 5.65; N, 8.26. Found: C, 67.61; H, 5.43; N, 8.28.

EXAMPLE 41

(17-Hydroxy-3-oxo-17α-pregn-4,6-diene-21-carboxalato)$_{2n}$-(aqua)$_{2n}$-copper (II)$_{n'}$[Cu(II)$_n$(17-1hydroxy-3-oxo-17α-pregn-4,6-diene-21-carboxylato)$_{2n}$(H$_2$O)$_{2n}$ The potassium salt of the parent acid (17-hydroxy-3-oxo-17α-pregn-4,6-diene-21-carboxylic acid) (5 g,0.013 mol) was dissolved in 50 ml of water. This solution was dropped into a stirred solution of cupric acetate monohydrate, prepared by dissolving 5 g (0.012 mol) in 50 ml of water. After the addition was completed the mixture was left to stir for an additional one-half hour before removing the precipitate by filtration. This precipitate was washed with 500 of water before air drying followed by drying at 30° and 15 mm Hg over the weekend. A 5 g, 24% yield was obtained. A sample of this material decomposed on heating over the range of 168°-169° C. This material was redried at 40° and 15 mm Hg before obtaining elemental analysis. Analysis Calcd. for $C_{88}H_{128}O_{22}Cu_2$: C, 64.88; H, 7.67. Found: C, 64.44; H, 7.87.

Inflammation Test Models Employed

In order to test the anti-inflammatory activities of my copper coordination compounds, the following test models were employed:

(1) Carrageenin Foot Edema Model as described in Experentia, 6, pp. 469-71, "Zur Frage des Mechanis Mos der Hemmung des Bindegebswachstums durch Cortisone" (1950);

(2) Cotton Wad Granuloma Model as described in J. Parmacol. Expt'l. Ther., 141, pp. 369-76, "Anti-inflammatory and Antipyretic Activities of Indomethacin, 9-(p-chlorobenzoyl)-5-Methoxy-2-Methyl-Indole-3-Acetic Acid" (1963); and (3) Polyarthritis Model as described in Nature, 224, pp. 1320-21, "Effect of Prostaglandin E$_2$ on Adjuvant Arthritis" (1969).

The foregoing literature references were followed in the following tests unless otherwise state and they are incorporated by reference herein. Each test model will only be briefly described. Each test model is a recognized and accepted model for testing drugs for the treatment of arthritis.

Carrageenin Foot Edema Model

In this test model test rats were injected with carrageenin in a hind paw one hour after administration of the copper coordination compound. The carrageenin induced inflammation. The rats were male, of the Sprague Dawley variety and weighed on the average 120 grams. The copper coordination compounds were first introduced subcutaneously. The dosages were compounded as follows:

TABLE A

| Copper Coordination Compound Weight in Milligrams | Saline Solution | Suspending Agent |
|---|---|---|
| 0.5 | 0.2 ml | several drops per 10 ml |
| 1 | 0.2 ml | |
| 2 | 0.2 ml | |
| 5 | 0.2 ml | |
| 25 | 0.2 ml | |

The suspending agent was Tween 80, a nonionic surfactant sold by the Atlas Posder Company. A full description of its is contained at p. 648 of Remingtons Practice of Pharmacy (11th ed., Martin & Cook, the Mack Publishing Co., Easton Pa. 1956). Generally they may be described as a complex mixture of polyoxyethylene ethers of mixed oleic esters of sorbitol anhydrides. The initial screening dosage was 25 mg of the copper coordination compound give in one injection to ten rats. Compounds which were active received further testing at 5.0 mg and lower dosages. Each dosage was administered to at least ten rats. A dose was rated active if it caused a significant decrease ($P<0.05$) in the circumference of the feet injected with carrageenin six hours after administration. Compounds were rated active if they possessed a subcutaneous potency of $\geqq 1\%$. As a reference standard, saline solution plus suspending agent was subcutaneously administered to each of the ten rats.

Cotton Wad Granuloma

This test utilizes the discovery that when cotton is introduced subcutaneously into a rat's skin it becomes encapsulated with connective tissue forming a granuloma. This is a manifestation of a local inflammatory response.

The rats utilized were male, of the Sprague Dawley variety and weighed on the average 175-200 gm. The rats were given an adrenalectomy one day prior to implantation. The cotton pellets, sterilized, each weighing 32-50 mg but for each experiment not varying ±1 mg. were inserted in each animal adjacent to the abdomen. The copper coordination compounds were subcutaneously introduced in various dosages daily for two days. The dosages were prepared in accordance with Table A and the description given in explanation thereof. Each dose was administered to at least ten rats. The initial screening dose was 20 mg. The compounds were rated active if they caused a significant decrease ($P<0.05$) in the adjusted weight of the granuloma tissue encapsulating the implanted cotton. In order to arrive at the adjusted weight a reference standard, hydrocortisone, 0.5 mg. was administered subcutaneously to ten reference standard rats. After two days, the rats, in the test model and reference standard were sacrificed and the granulomas from each were removed, weighed, dried and reweighed. The adjusted weights were calculated as wet granuloma from test model compared to wet granuloma from reference standard and dry granuloma from test model compared to dry granuloma from reference standard.

Polyarthritis Model

In this model the test rats, male Sprague Dawley rats, 160-180 g, were inoculated intradermally at the base of the tail with a Freund type adjuvant as described in Nature, supra, to wit: 0.6 mg dry, heat-killed Mycobacterium butyricum (purchased from Difco) suspended in 0.05 ml of paraffin oil. The test rats were injected subcutaneously daily for 16 days with varying dosages of copper coordination compound prepared by mixing the copper compound with saline solution and suspending agent in the proportion set forth in Table A and in the manner described in connection therewith. The initial screening dose was 5 mg. Each dose was administered to at least twelve rats. As a control group, twelve rats were also injected subcutaneously with saline solution plus suspending agent.

On day 16 (day 1=day of inoculation) the rats were sacrificed. The circumference of the tibiotarsal (ankle) joint was used as a measure of the severity of the inflammation. Table I and Table IV set forth the results of the foregoing tests and Table I includes in addition comparisons of the anti-inflammatory activities of my compounds vs. hydrocortisone.

Ulcer Test Models Employed

To determine the ulcergenicity of my copper coordination compounds, two different test models were employed—the Shay rat test and the Corticoid Induced Rat Ulcer Test. These are commonly employed tests described in the literature. Shay, et al, "A Simple Method for the Uniform Production of Gastric Ulceration in the Rat, " *Gastroenterology* 5, 43-61 1945); and Robert, A. et al, Proc. Soc. Expt'l. Biol. 99, pp. 443-47, "Ulcergenic Properties of Steroids" (1958), incorporated by reference herein.

Shay Rat Test

The procedure set forth in the above described method by Shay et al. was followed. The rats were males of the Sprague Dawley variety, weighing 200-250 grams, which had been fasted for 72 hours. The control group of twelve rats received a saline and Tween 80 solution introduced intragastrically. An initial screening dose of 50 mg copper coordination compound, mixed with saline solution and Tween 80 suspending agent was introduced intragastrically into twelve rats. If the compounds displayed activity, as determined in the manner described below, dosages of either 0.5 mg, 1 mg, 2.5 mg, or 10 mg were administered. Each dose was given to at least twelve rats. The following Table B shows how the dosages were formulated.

TABLE B

| Copper Compound (mg) | Saline Solution ML | Suspending Agent |
|---|---|---|
| 0.5 | 1 | 1 drop |
| 1 | 1 | 1 drop |
| 2.5 | 1 | 1 drop |
| 10 | 1 | 1 drop |
| 50 | 1 | 1 drop |

The activity of the dosages was arrived at by sacrificing the rats after 19 hours and determining the size and number of ulcers present. The incidence of ulcers in rats receiving the dosages of copper compounds were compared with the incidence of ulcers in rats in the control group. The compounds were rated active if the comparison showed that the compound significantly inhibited ulceration ($P < 0.05$).

Corticoid-Induced Rat Ulcer Test 8 mg of $\Delta^1$-cortisol in about 0.2 ml corn oil was injected subcutaneously into each rat in two groups of male Sprague Dawley rats (about 150 to 165 g) daily for four days. The rats in the control group received no other compound, while the rats in the treated group received orally 25 mg of various copper coordination compounds of my invention (1 ml saline solution - 1 drop Tween 80) three times daily.

The results of this test, using the ulcer index as found in Robert, A. et al, Proc. Soc. Expt'l. Biol. 99, pp. 443–47, "Ulcergenic Property of Steroids" (1958) (incorporated by reference herein) are included in Tables III and IV.

In addition to the foregoing anti-inflammatory and anti-ulcer tests, several $LD_{50}$ tests [performed in accordance with Miller et al, Proceed. of the Society of Expt'l. Medicine, 57, p. 261 (1944)] were performed with some copper coordination compounds and compared to cupric acetate, aspirin and tpan. The results are set forth in Table II along with TI data which is the ratio of the lethal dose to effective dose.

The following surprising results may be gleaned quickly by reviewing the results set forth in Tables I-IV.

(1) A marked increase in anti-inflammatory activity was observed for most of the compounds of the present invention as compared to prior art compounds.

(2) Many parent compounds used to prepare the copper coordination compounds possessed no anti-inflammatory activity while their copper coordination compounds did.

(3) The $LD_{50}$ of the copper coordination compounds of my invention were substantially less than prior art anti-inflammatory agents.

(4) While all known prior art compounds useful as anti-inflammatory agents are known ulcergenic compounds, my copper coordination compounds displayed anti-ulcer activity.

Upon further and more extensive study of the results the following observations are of interest to those skilled in the art.

From a review of the Tables it can be noted that activity in the various test models is apparently not a function of the amount of the percent of copper present in the copper coordination compound. For example, activity in the Shay Rat Anti-Ulcer activity model was displayed in compounds at similar dosages having about 7.7% be weight copper and in compounds having about 19% by weight copper.

While examples 1, 8, 16, 30 and 41 showed no anti-inflammatory activity at the initial screening tests and using only one test model, it is believed that they would display anti-inflammatory activity under other conditions.

From the foregoing description it can be noted that all of the compounds of the present invention have the formula $Cu_yX_n$ wherein y and n are numerals and wherein x is derived from at least one group of coordinating elements. By group of coordinating elements I means a group of elements which are not attached to each other in a cyclic manner. The coordinating compounds may contain within them carbocyclic or heterocyclic structural components. By coordinating elements I means elements which contribute electrons to form a covalent bond with copper, which may have a valence state of $+1$ or $+2$. In most instances, such coordinating elements are selected from the group of oxygen, nitrogen, halogen and sulfur.

In most instances my copper coordination compounds have the formula $Cu_{1y}X_{2n}$. In this case the coordinating groups may be the same or different. Another class of my copper coordination compounds has the formula $Cu_{3y}X_{2n}$ and the coordinating groups may be the same or different. A still further class has the formula $Cu_{2y}X_{4n}$ and the coordinating groups may be the same or different.

From the foregoing description it will also be understood that in the treatment of inflammation (arthritis) and gastrointestinal ulcers in animals my compounds may be administered in customary ways. While the dosages recommended herein for use are preferred other dosages may also provide beneficial results.

Referring now to Table V, which sets out some of the structural formulae of my copper coordination compounds, the following is given in explanation thereof.

Example 1 has the structure d when the ligand is derived from L-tryptophan (a) and x is a amino. Example 2 has the structure d when the ligand is derived from D-tryptophan (a) and x is amino. Example 16 has the structure d when the ligand is derive from D,L-tryptophan (a) and x is amino. Example 3 has the structure d when the ligand is derived from anthranilic acid (b) and x is o-amino.

Example 4 has the structure d when the ligand is derived from 3,5-diisopropylsalicylic acid (c) and x is o-hydroxy.

TABLE I

THE ANTI-INFLAMMATORY ACTIVITIES OF SOME COPPER COORDINATION COMPOUNDS COMPARED WITH SOME OF THEIR PARENT COMPOUNDS

| EXAMPLE | COMPOUND | CARRAGEENIN FOOT EDEMA | COTTON WAD GRANULOMA | POLYARTHRITIS | % POTENCY COMPARED WITH HYDRO-CORTISONE | % COPPER |
|---|---|---|---|---|---|---|
| | cupric acetate | A @ 1 mg SC | I @ 20 mg SC | I @ 5 mg SC | 340 | 31.8 |
| | L-tryptophan | I @ 25 mg SC | NT | NT | | |
| 1 | Cu(II)(L-tryptophan)$_2$ | I @ 25 mg SC | I @ 20 mg SC | NT | | 13.5 |
| | D-tryptophan | I @ 25 mg SC | NT | NT | | |
| 2 | Cu(II)(D-tryptophan)$_2$ | A @ 25 mg SC | I @ 20 mg SC | NT | | 13.5 |
| | anthranilic acid | I @ 25 mg SC | NT | I @ 5 mg SC | | |
| 3 | Cu(II)(anthranilate)$_2$ | A @ 1 mg SC | A @ 5 mg SC | A @ 0.2 mg SC(+25) | 60 | 18.9 |
| | 3,5-dips acid | I @ 25 mg SC | NT | I @ 5 mg SC | | |
| 4 | Cu(II)(3,5-dips)$_2$ | A @ 1 mg SC | A @ 1 mg SC | A @ 0.2 mg SC(+24) | 50 | 12.5 |

TABLE I-continued
THE ANTI-INFLAMMATORY ACTIVITIES OF SOME COPPER COORDINATION COMPOUNDS COMPARED WITH SOME OF THEIR PARENT COMPOUNDS

| EXAMPLE | COMPOUND | CARRAGEENIN FOOT EDEMA | COTTON WAD GRANULOMA | POLYARTHRITIS | % POTENCY COMPARED WITH HYDROCORTISONE | % COPPER |
|---|---|---|---|---|---|---|
|  | aspirin | A @ 8 mg SC | A @ 40 mg IG | A @ 1 mg SC(+5) | 6 |  |
| 5 | $Cu(II)_2(aspirinate)_4$ | A @ 1 mg SC | A @ 2 mg SC | A @ 0.2 mg SC(+27) | 130 | 15.0 |
|  | tpan | A @ 5 mg IG | A @ 5 mg IG | A @ 1 mg IG(+5) | 31 |  |
| 6 | $Cu(II)_n(tpan)_{2n}(H_2O)_n$ | A @ 1 mg SC | A @ 2 mg SC | A @ 0.2 mg SC(+18) | 180 | 10.1 |
|  | D-penicillamine | I @ 25 mg SC | I @ 20 mg SC | I @ 5 mg SC |  |  |
| 7 | $Cu(I)_nD\text{-pen}(H_2O)_{1.5n}$ | A @ 1 mg SC | A @ 2 mg SC | NT |  | 26.7 |
| 8 | $Cu(II)_n(D\text{-pen})_{2n}(H_2O)_{2n}$ | I @ 25 mg SC | NT | NT |  | 16.1 |
| 9 | $Cu(II)_n(D\text{-pen disulfide})_n(H_2O)_{3n}$ | A @ 1 mg SC | A @ 5 mg SC | A @ 5 mg SC(+18) |  | 15.4 |
|  | pat | I @ 25 mg SC | A @ 20 mg IG | A @ 20 mg IG(+5) |  |  |
| 10 | $Cu(II)_n(pat)_n(acetate)_{2n}$ | A @ 1 mg SC | A @ 5 mg SC | A @ 5 mg SC(+5) |  | 18.5 |
| 11 | $Cu(II)_n(pat)_{2n}(HCl)_{2n}$ | A @ 2 mg SC | A @ 2 mg SC | NT |  | 13.9 |

TABLE II
THE $LD_{50}$ AND CALCULATED TI DATA FOR SOME COPPER COORDINATION COMPOUNDS

| EXAMPLE | COMPOUND | $LD_{50}$ | TI CFE | TI PA |
|---|---|---|---|---|
|  | cupric acetate | 350 mpk SC | 70 | 0 |
| 3 | $Cu(II)(anthranilate)_2$ | 750 ± 106 mpk SC | 150 | 750 |
| 4 | $Cu(II)(3,5\text{-dips})_2$ | 240 ± 33 mpk SC | 48 | 240 |
|  | aspirin | 1500 mpk IG |  |  |
|  |  | 790 mpk RT |  |  |
| 5 | $Cu(II)_2(aspirinate)_4$ | 760 ± 100 mpk SC | 150 | 760 |
|  | tpan | 370 ± 25 mpk IG | 15 | 74 |
| 6 | $Cu(II)_n(tpan)_{2n}(H_2O)_n$ | 650 ± 80 mpk SC | 130 | 650 |

TABLE III
A COMPARISON OF THE ANTI-ULCER ACTIVITIES AMONG THE COPPER COORDINATION COMPOUNDS OF TABLE I AND SOME OF THEIR PARENT COMPOUNDS

| EXAMPLE | COMPOUND | SHAY RAT: ANTI-ULCER ACTIVITY | CORTICOID INDUCED: ANTI-ULCER ACTIVITY |
|---|---|---|---|
|  | $Cu(II)_2(acetate)_4(H_2O)_2$ | A @ 50 mg IG | NT |
| 1 | $Cu(II)(L\text{-tryptophan})_2$ | A @ 0.1 mg IG | A @ 25 mg IG |
| 2 | $Cu(II)(D\text{-tryptophan})_2$ | A @ 1 mg IG | NT |
|  | D-tryptophan | I @ 50 mg IG | NT |
| 3 | $Cu(II)(anthranilate)_2$ | A @ 1 mg IG | A @ 25 mg IG |
|  | anthranilic acid | A @ 50 mg IG | NT |
| 4 | $Cu(II)(3,5\text{-dips})_2$ | A @ 0.5 mg IG | A @ 25 mg IG |
| 5 | $Cu(II)_2(aspirinate)_4$ | A @ 2.5 mg IG | NT |
|  | aspirin | A @ 50 mg IG | NT |
| 6 | $Cu(II)_n(tpan)_{2n}(H_2O)_n$ | A @ 1 mg IG | NT |
|  | tpan | I @ 50 mg IG | NT |
| 7 | $Cu(I)_nD\text{-pen}(H_2O)_{1.5n}$ | NT | NT |
| 8 | $Cu(II)_n(D\text{-pen})_{2n}(H_2O)_{2n}$ | A @ 1 mg IG | NT |
| 9 | $Cu(II)_n(D\text{-pen disulfide})_n(H_2O)_{3n}$ | A @ 1 mg IG | NT |
| 10 | $Cu(II)_n(pat)_n(acetate)_{2n}$ | A @ 1 mg IG | NT |
| 11 | $Cu(II)_n(pat)_{2n}(HCl)_{2n}$ | A @ 1 mg IG | NT |

TABLE IV
THE ANTI-INFLAMMATORY AND ANTI-ULCER ACTIVITIES OF SOME ADDITIONAL COPPER COORDINATION COMPOUNDS COMPARED TO SOME OF THEIR PARENT COMPOUNDS

| EXAMPLE | COMPOUND | CARRAGEENIN FOOT EDEMA | COTTON WAD GRANULOMA | POLYARTHRITIS |
|---|---|---|---|---|
|  | Amino Acids |  |  |  |
|  | $Cu(II)_n(D\text{-aspartate})_n(H_2O)_{3.5n}$ | A @ 1 mg SC | A @ 2 mg SC | NT |
|  | $Cu(II)_n(L\text{-aspartate})_n(H_2O)_{3.5n}$ | A @ 1 mg SC | NT | NT |
|  | $Cu(II)_n(L\text{-lysinate})_n(Cl)_{2n}(H_2O)_n$ | A @ .5 mg SC | A @ 2 mg SC | NT |
|  | $Cu(II)_n(L\text{-lysinate})_{2n}(Cl)_{2n}(H_2O)_n$ | A @ 1 mg SC | NT | NT |
| 16 | $Cu(II)(D,L\text{-tryptophan})_2$ | I @ 25 mg SC | NT | NT |
| 17 | $Cu(II)_n(\epsilon\text{-aminocaproate})_n(Cl)_{1.5n}(CH_3OH)_{0.5n}$ | NT | NT | NT |
| 18 | $Cu(II)_n(\epsilon\text{-aminocaproate})_n(Cl)_{2n}(H_2O)_{0.5n}$ | NT | NT | NT |
|  | Amines |  |  |  |
| 19 | $Cu(II)_2(pyridine)_2(acetate)_4$ | A @ 2 mg SC | NT | NT |
| 20 | $Cu(II)(pyridine)_2(Cl)_2$ | A @ 1 mg SC | NT | NT |
| 21 | $Cu(II)(morpholine)_2(Cl_2)(HCl)_2$ | A @ 0.5 mg SC | A @ 5 mg SC | NT |
| 22 | $Cu(II)_n(histamine)_n(Cl)_{2n}(HCl)_{2n}$ | NT | NT | NT |

TABLE IV-continued
THE ANTI-INFLAMMATORY AND ANTI-ULCER ACTIVITIES OF SOME ADDITIONAL COPPER COORDINATION COMPOUNDS COMPARED TO SOME OF THEIR PARENT COMPOUNDS

|  | Compound | | | |
|---|---|---|---|---|
|  | Salicylates | | | |
|  | $Cu(II)_2(salicylate)_4(Na)_4$ | A @ 2 mg SC | A @ 2 mg SC | NT |
|  | $Cu(II)_n(salicylate)_{2n}(H_2O)_{4n}$ | A @ 1 mg SC | A @ 5 mg SC | NT |
|  | Heterocyclic Carboxylic Acids | | | |
| 25 | $Cu(II)_{2n}(nicotinate)_{4n}(H_2O)_{3n}$ | NT | NT | NT |
| 26 | $Cu(II)_n(1\text{-carboxyisoquinoline})_{2n}$ | A @ 5 mg SC | A @ 5 mg SC | NT |
| 27 | $Cu(II)_n(2\text{-phenyl-4-carboxyisoquinoline})_{2n}(H_2O)_{2n}$ | NT | NT | NT |
| 28 | $Cu(II)_n(2\text{-carboxyindole})_{3n}(acetate)_n(H_2O)_{0.5n}$ | A @ 1 mg SC | A @ 2 mg SC | NT |
| 29 | $Cu(II)_n(2\text{-carboxyindole})_{3n}(acetate)_n(H_2O)_{3.5n}$ | NT | NT | NT |
| 30 | $Cu(II)_n(\text{cp-tcca})_{2n}(H_2O)_{2n}$ | I @ 25 mg SC | NT | NT |
| 31 | $Cu(II)_n(\text{tcca})_{2n}(H_2O)_{2.5n}$ | I @ 5 mg SC | NT | NT |
|  | Corticoids | | | |
|  | hydrocortisone-21-phophate(Na)$_2$ | NT | NT | I @ 1 mg SC** |
| 32 | $Cu(II)_{3n}(\text{HC-31-phosphate})_{2n}(H_2O)_{9n}$ | A @ 2 mg SC | A @ 5 mg SC | A @ 1 mg SC(+7)** |
| 33 | $Cu(II)_{3n}(\text{HC-21-phosphate})_{2n}(H_2O)_{7n}$ | NT | NT | I @ 1 mg SC** |
|  | hydrocortisone-21-hemisuccinate | NT | NT | A @ 1 mg SC(+7)** |
| 34 | $Cu(II)_{2n}(\text{HC-21-hemisuccinate})_{4n}(H_2O)_{6n}$ [Green] | A @ 2 mg SC | A @ 5 mg SC | A @ 1 mg SC(+7)** |
| 35 | $Cu(II)_{2.5n}(\text{HC-21-hemisuccinate})_{2n}(H_2O)_{7n}$ [Blue] | A @ 2 mg SC | A @ 1 mg SC | A @ 1 mg SC(+11)** |
|  | Dexamethasone-21-phosphate(Na)$_2$ | NT | NT | NT |
| 36 | $Cu(II)_{3n}(\text{dexamethasone-21-phosphate})_{2n}(H_2O)_{7n}$ | NT | NT | NT |
| 37 | $Cu(II)_{3n}(\text{desamethasone-21-phosphate})_{2n}(H_2O)_{1.5n}$ | NT | NT | NT |
|  | Arylacetic Acids | | | |
| 38 | $Cu(II)_{2n}[1\text{-(p-chlorobenzoyl)-5-methoxy-2-methylindole-3-acetate}]_{4n}(H_2O)_{4n}$ | NT | NT | NT |
| 39 | $Cu(II)_{2n}[1\text{-(p-chlorobenzoyl)-5-methoxy-2-methylindole-3-acetate}]_{4n}(CH_3COCH_3)_{2n}$ | NT | NT | NT |
|  | Pyrazolidinedione | | | |
| 40 | $Cu(II)_n(4\text{-n-butyl-1,2-diphenyl-3,5-pyrazolidinedione})_{2n}$ | NT | NT | NT |
|  | Steroidal Acids | | | |
| 41 | $Cu(II)_n(17\text{-hydroxy-3-oxo-17-pregn-4,6-diene-21-carboxalate})_{2n}(H_2O)_{2n}$ | I @ 5 mg SC** | NT | I @ 5 mg SC** |

| EXAMPLE | COMPOUND | PERCENT COPPER | SHAY RAT: ANTI-ULCER ACTIVITY |
|---|---|---|---|
|  | Amino Acids | | |
|  | $Cu(II)_n(\text{L-aspartate})_n(H_2O)_{3.5n}$ | 32.6 | A @ 0.5 mg IG |
|  | $Cu(II)_n(\text{L-lysinate})_n(Cl)_{2n}(H_2O)_n$ | 21.9 | A @ 10 mg IG |
|  | $Cu(II)_n(\text{L-lysinate})_{2n}(Cl)_{2n}(H_2O)_n$ | 14.3 | NT |
| 16 | $Cu(II)(D,L\text{-tryptophan})_2$ | 13.5 | A @ 1 mg IG |
| 17 | $Cu(II)_n(\epsilon\text{-aminocaproate})_n(Cl)_{1.5n}(CH_3OH)_{0.5n}$ | 24.0 | A @ 2.5 mg IG |
| 18 | $Cu(II)_n(\epsilon\text{-aminocaproate})_n(Cl)_{2n}(H_2O)_{0.5n}$ | 23.2 | A @ 1 mg IG* |
|  | Amines | | |
| 19 | $Cu(II)_2(\text{pyridine})_2(acetate)_4$ | 24.4 | A @ 0.5 mg IG |
| 20 | $Cu(II)(\text{pyridine})_2(Cl)_2$ | 21.6 | A @ 10 mg IG |
| 21 | $Cu(II)(\text{morpholine})_2(Cl_2)(HCl)_2$ | 16.6 | NT |
| 22 | $Cu(II)_n(\text{histamine})_n(Cl)_{2n}(HCl)_{2n}$ | 20.0 | A @ 10 mg IG* |
|  | Salicylates | | |
|  | $Cu(II)_2(\text{salicylate})_4(Na)_4$ | 17.8 | NT |
|  | $Cu(II)_n(\text{salycylate})_{2n}(H_2O)_{4n}$ | 15.5 | A @ 1 mg IG |
|  | Heterocyclic Carboxylic Acids | | |
| 25 | $Cu(II)_{2n}(\text{nicotinate})_{4n}(H_2O)_{3n}$ | 19.0 | A @ 1 mg IG |
| 26 | $Cu(II)_n(1\text{-carboxyisoquinioline})_{2n}$ | 15.6 | A @ 50 mg IG |
| 27 | $Cu(II)_n(2\text{-phenyl-4-carboxyisoquinoline})_{2n}(H_2O)_{2n}$ | 10.6 | A @ 1 mg IG* |
| 28 | $Cu(II)_n(2\text{-carboxylindole})_{3n}(acetate)_n(H_2O)_{0.5n}$ | 16.5 | A @ 0.5 mg IG |
| 29 | $Cu(II)_n(2\text{-carboxylindole})_{3n}(acetate)_n(H_2O)_{3.5n}$ | 15.4 | A @ 1 mg IG* |
| 30 | $Cu(II)_n(\text{cp-tcca})_{2n}(H_2O)_{2n}$ | 8.8 | A @ 1 mg IG |
| 31 | $Cu(II)_n(\text{tcca})_{2n}(H_2O)_{2.5n}$ | 11.8 | A @ 50 mg IG |
|  | Corticoids | | |
|  | hydrocortisone-21-phosphate(Na)$_2$ | | I @ 10 mg IG** |
| 32 | $Cu(II)_{3n}(\text{HC-21-phosphate})_{2n}(H_2O)_{9n}$ | 15.4 | A @ 5 mg IG |
| 33 | $Cu(II)_{3n}(\text{HC-21-phosphate})_{2n}(H_2O)_{7n}$ | 15.9 | A @ 2.5 mg IG |
|  | hydrocortisone-21-hemisuccinate | | I @ 10 mg IG** |
| 34 | $Cu(II)_{2n}(\text{HC-21-hemisuccinate})_{4n}(H_2O)_{6n}$ [Green] | 6.1 | A @ 5 mg IG |
| 35 | $Cu(II)_{2.5n}(\text{HC-21-hemisuccinate})_{2n}(H_2O)_{7n}$ [Blue] | 13.5 | A @ 10 mg IG* |
|  | Dexamethasone-21-phosphate(Na)$_2$ | | NT |
| 36 | $Cu(II)_{3n}(\text{dexamethasone-21-phosphate})_{2n}(H_2O)_{7n}$ | 15 | A @ 5 mg IG |
| 37 | $Cu(II)_{3n}(\text{dexamethasone-21-phosphate})_{2n}(H_2O)_{1.5n}$ | 16 | A @ 5 mg IG |
|  | Arylacetic Acids | | |
| 38 | $Cu(II)_{2n}[1\text{-(p-chlorobenzoyl)-5-methoxy-2-methylindole-3-acetate}]_{4n}(H_2O)_{4n}$ | 7.8 | A @ 10 mg IG* |
| 39 | $Cu(II)_{2n}[1\text{-(p-chlorobenzoyl)-5-methoxy-2-methylindole-3-acetate}]_{4n}(CH_3COCH_3)_{2n}$ | 7.7 | A @ 1 mg IG |
|  | Pyrazolidineione | | |
| 40 | $Cu(II)_n(4\text{-n-butyl-1,2-diphenyl-3,5-pyrazolidinedione})_{2n}$ | 11.8 | A @ 10 mg IG |

TABLE IV-continued

THE ANTI-INFLAMMATORY AND ANTI-ULCER ACTIVITIES OF SOME ADDITIONAL COPPER COORDINATION COMPOUNDS COMPARED TO SOME OF THEIR PARENT COMPOUNDS

| | | Steroidal Acids | | |
|---|---|---|---|---|
| | 41 | $Cu(II)_n$(17-hydroxy-3-oxo-17-pregn-4,6-diene-21-carboxalate)$_{2n}$(H$_2$O)$_{2n}$ | 7.8 | A @ 5 mg IG |

*Not tested at lower dose
**Only dose tested
NT = Not Tested

TABLE V

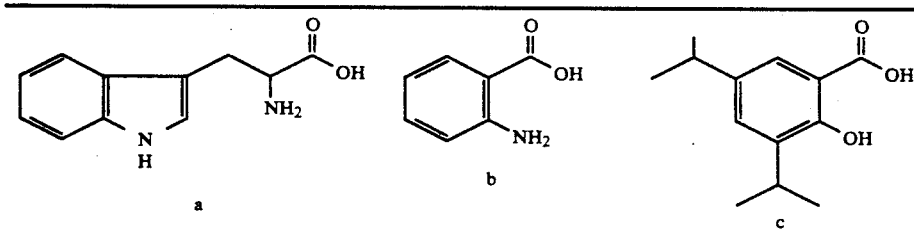

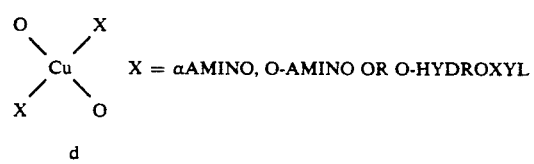

X = αAMINO, O-AMINO OR O-HYDROXYL d

EXAMPLES 1, 2, 16; 3 and 4.

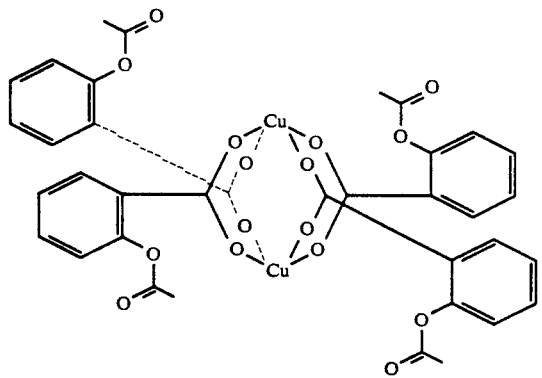

EXAMPLE 5

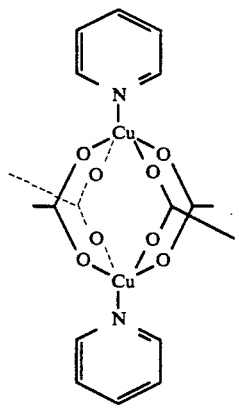

EXAMPLE 19

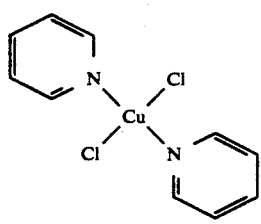

EXAMPLE 20

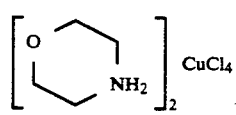

EXAMPLE 21

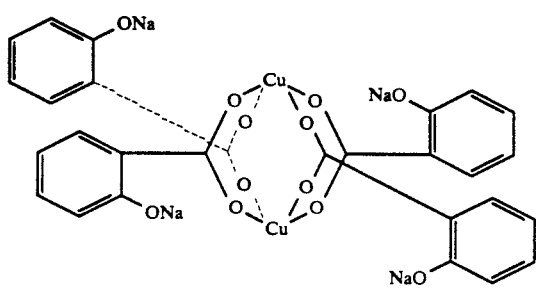

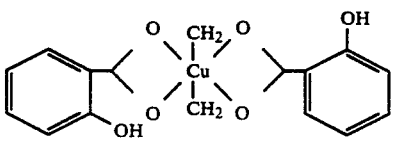

I claim:

1. A process for treating arthritis in an animal body while reducing the likelihood of producing ulcers, consisting essentially of:
   administering to said animal body, orally or parenterally, a copper coordination compound having anti-ulcergenic properties having anti-ulcergenic properties selected from the group consisting of Bis(3,5-diisopropylsalicylate(O,O)copper (II)[Cu(II)(3,5-dips)$_2$], Tetra(u-acetylsalicylato)biscopper(II),-[Cu(II$_2$(aspirinate)$_4$], and (Salicylato)$_{2n}$-(aqua)$_{4n}$-copper(II)$_n$·[Cu(II) (Salicylate)$_2$ (H$_2$O)$_4$], wherein n is a number, the amount of said copper coordination compound administered to said animal body being about 2.5 to 165 mg per kilogram of body weight.

2. The process of claim 1 wherein said copper coordination compound is (Salicylato)$_{2n}$-(aqua)$_{4n}$-copper(II)$_{n'}$·[Cu(II)(Salicylate)$_2$(H$_2$O)$_4$].

3. A process for treating inflamation in an animal body consisting essentially of:
   administering to said animal body a copper coordination compound having anti-ulcergenic properties comprising the reaction product of a copper salt with an aromatic carboxylic acid or the alkaline earth salts thereof, the amount of said copper coordination compound administered to said animal body being about 0.1 to 500 mg per kilogram of body weight.

4. The process of claim 3 wherein the copper salt is selected from the group consisting of cupric chloride and cupric acetate.

5. The process of claim 4 wherein the copper coordination compound is selected from the group consisting of Bis(3,5-diisopropylsalicylate (O,O) copper (II [Cu(II) (3,5-dips)$_2$-], Tetra(u-acetylsalicylato)biscopper(II), (CuII)$_2$ (Acetyl-salicylate)$_4$ and (Salicylat)$_{2n}$-(aqua)$_{4n}$-copper(II)$_{n'}$·[CU(II) (Salicylate)$_2$ (H$_2$O)$_4$]wherein n is a number.

6. The process of claim 3 wherein the aromatic carboxylic acid is selected from the group consisting of 3,5-diisopropylsalicylic acid, acetylsalicylic acid and salicylic acid.

7. The process of claim 3 wherein the acid is 3,5-diisopropylsalicylic acid.

8. The process of claim 3 wherein the acid is salicylic acid.

9. The process of claim 3 wherein the acid is acetylsalic acid.

* * * * *

UNITED STATES PATENT AND TRADEMARK OFFICE
CERTIFICATE OF CORRECTION

PATENT NO. : 5,082,834                              Page 1 of 2
DATED : January 21, 1992
INVENTOR(S) : John R. J. Sorenson It is certified that error appears in the above-indentified patent and that said Letters Patent is hereby corrected as shown below:

On the Title Page, item 54,     "Sorensen" should be --Sorenson--

On the Title Page, item 54     "John R. J. Sorensen" should be --John R. J. Sorenson--

Col. 4 Line 3     "Tetra$_\mu$" should be --Tetra($_\mu$--

Col. 9 Line 7     "(acetato)phd n-(aqua)" should be --acetato)$_n$-(Aqua)--

Col. 24 Line 17     "[CU(II)" should be --C$\mu$(II)--

Col. 2 Line 30     "heterocycline" should be --heterocyclic--

Col. 2 Line 45     "$\epsilon$" should be --$\epsilon^-$--

Col. 4 Line 6     "30 g, 0.165 mol" should be --56.5 g, 0.330 mol--

Col. 4 Line 11     "56.5 g, 0.330 mol" should be --30 g, 0.165 mol"--

UNITED STATES PATENT AND TRADEMARK OFFICE
CERTIFICATE OF CORRECTION

PATENT NO. : 5,082,834
DATED : January 21, 1992
INVENTOR(S) : John R. J. Sorenson It is certified that error appears in the above-indentified patent and that said Letters Patent is hereby corrected as shown below:

Col. 11 Line 62    "coordination was" should be --coordination compound was--

Col. 14 Line 32    "ulcergenicity" should be --anti-ulcergenicity--

Col. 24 Line 16    "(CuII)$_2$(Acetyl-salicylate)$_4$" should be --Cu(II)$_2$(Acetyl-salicylato)$_4$--

Col. 24 Line 28    "acetylsalic" should be --acetylsalicylic--

Signed and Sealed this

Second Day of August, 1994

Attest:

BRUCE LEHMAN

Attesting Officer    Commissioner of Patents and Trademarks